(12) United States Patent
Deng et al.

(10) Patent No.: US 9,095,336 B2
(45) Date of Patent: Aug. 4, 2015

(54) KNOTLESS SUTURE DEVICE

(75) Inventors: Meng Deng, Branchburg, NJ (US);
David Stoloff, Whitehouse Station, NJ (US); Robert Nering, Stockton, NJ (US); Lisa Baryschpolec, Clinton, NJ (US); Robert Vetrecin, Stewartsville, NJ (US)

(73) Assignee: Ethicon, Inc., Somerville, NJ (US)

( * ) Notice: Subject to any disclaimer, the term of this patent is extended or adjusted under 35 U.S.C. 154(b) by 717 days.

(21) Appl. No.: 12/642,441

(22) Filed: Dec. 18, 2009

(65) Prior Publication Data

US 2011/0152927 A1    Jun. 23, 2011

(51) Int. Cl.
*A61B 17/04*    (2006.01)
*A61B 17/06*    (2006.01)
*A61B 17/08*    (2006.01)

(52) U.S. Cl.
CPC ... *A61B 17/06166* (2013.01); *A61B 2017/0404* (2013.01); *A61B 2017/081* (2013.01)

(58) Field of Classification Search
CPC ............... A61B 17/06166; A61B 2017/0404; A61B 2017/081
USPC .......................... 606/128, 144, 148, 232, 228
See application file for complete search history.

(56) References Cited

U.S. PATENT DOCUMENTS

| | | | | | |
|---|---|---|---|---|---|
| 3,910,281 | A | * | 10/1975 | Kletschka et al. | 606/232 |
| 4,185,637 | A | * | 1/1980 | Mattei | 606/230 |
| 4,705,040 | A | * | 11/1987 | Mueller et al. | 606/108 |
| 5,449,367 | A | | 9/1995 | Kadry | |
| 2004/0084331 | A1 | * | 5/2004 | Roby et al. | 206/63.3 |
| 2006/0264347 | A1 | * | 11/2006 | Ming et al. | 510/161 |
| 2007/0135843 | A1 | * | 6/2007 | Burkhart | 606/232 |

* cited by examiner

*Primary Examiner* — Elizabeth Houston
*Assistant Examiner* — Christina Lauer
(74) *Attorney, Agent, or Firm* — E. Richard Skula

(57) ABSTRACT

A knotted suture device is disclosed. The device may have a surgical needle attached to one or both ends of the suture. The device has a plurality of loops formed by knots. An anchor member is attached to the device. The device when used in a surgical procedure can be secured without the need to tie a knot.

9 Claims, 19 Drawing Sheets

US 9,095,336 B2

KNOTLESS SUTURE DEVICE

TECHNICAL FIELD

The field of art to which this invention pertains is medical devices, more particularly, surgical sutures for approximating tissue.

BACKGROUND OF THE INVENTION

Surgical sutures are well known medical devices used by physicians and surgeons in a variety of conventional surgical procedures and for various applications, including the approximation of tissue about wounds, securing other medical devices such as heart valves or catheters to tissue, connecting blood vessels, ligating blood vessels, approximating soft tissue and bone, etc. The sutures are typically attached on one or both ends to conventional surgical needles. The surgical needles are used to pierce and penetrate tissue and create a pathway in the tissue for the suture to pass through. In a typical surgical procedure, numerous passes of the needle and suture through tissue about the wound are often needed for complete tissue approximation. In order to properly secure the suture in tissue, it is necessary to knot the ends of the suture so that, subsequent to the procedure, when the approximated tissue pulls on the suture it will remain substantially in place. This is critical for the healing process.

Relatively recently, minimally invasive surgical procedures have been introduced and have replaced many conventional, open procedures. Examples of minimally invasive procedures include cholecystectomies, appendectomies, arthroscopic repairs to joints, laparoscopic surgery, microsurgery, and thoracoscopic surgery. In a conventional minimally invasive procedure, the surgical site is accessed with trocar to emplace trocar cannulas. The trocar cannulas provide a relatively small opening and pathway to the surgical site. The size of such openings is dependent upon the nature of the procedure and the characteristics of the surgical site, may typically range, for example, from 5 mm to 12 mm. The trocar cannulas provide pathways to and from the surgical site for surgical instruments, and for scopes to provide the surgeon with a remote image of the site. Specially designed endoscopic, laparoscopic or arthroscopic instruments are used in such minimally invasive procedures. The instruments typically have elongated shafts with the operable functional instrument members on the distal ends, which are controllable by a handle or controller on the proximal end. It is necessary that the shaft and the distal working end, or so-called "business end", have small profiles in order to readily fit through a cannula and access the surgical site, and to provide for maneuverability by the surgeon during the procedure.

One difficulty encountered in minimally invasive surgical procedures is approximating tissue at the surgical site using surgical needles and sutures. This has been addressed by special endoscopic suture instruments which allow the surgeon to pass surgical needles through tissue while working through cannulas and viewing the site remotely on a visual display. This is often a difficult and time-consuming procedure even with these specially designed instruments, and the knotting or securing of the suture after the tissue approximation has been completed has been especially challenging. It would be advantageous to have sutures that could be secured in a minimally invasive procedure without the need for the surgeon to tie knots.

Accordingly, there is a need in this art for novel surgical sutures useful in minimally invasive surgical procedures having the capability of being readily secured in tissue without the need for tying surgical knots after emplacement in tissue.

SUMMARY OF THE INVENTION

Accordingly, a novel suture useful in minimally invasive procedures is disclosed. The surgical suture device has a suture strand. The suture strand has a proximal end and a distal end, and the suture strand contains a plurality of spaced apart knots to create a plurality of suture loops including an end loop. Each suture loop has an opening and first and second suture segments. There is an anchor member mounted to the end loop.

Yet another aspect of the present invention is a method of approximating mammalian tissue using the above-described device.

These and other aspects of the present invention will become more apparent by the following description and accompanying drawings.

DETAILED DESCRIPTION OF THE INVENTION

Figure 1:
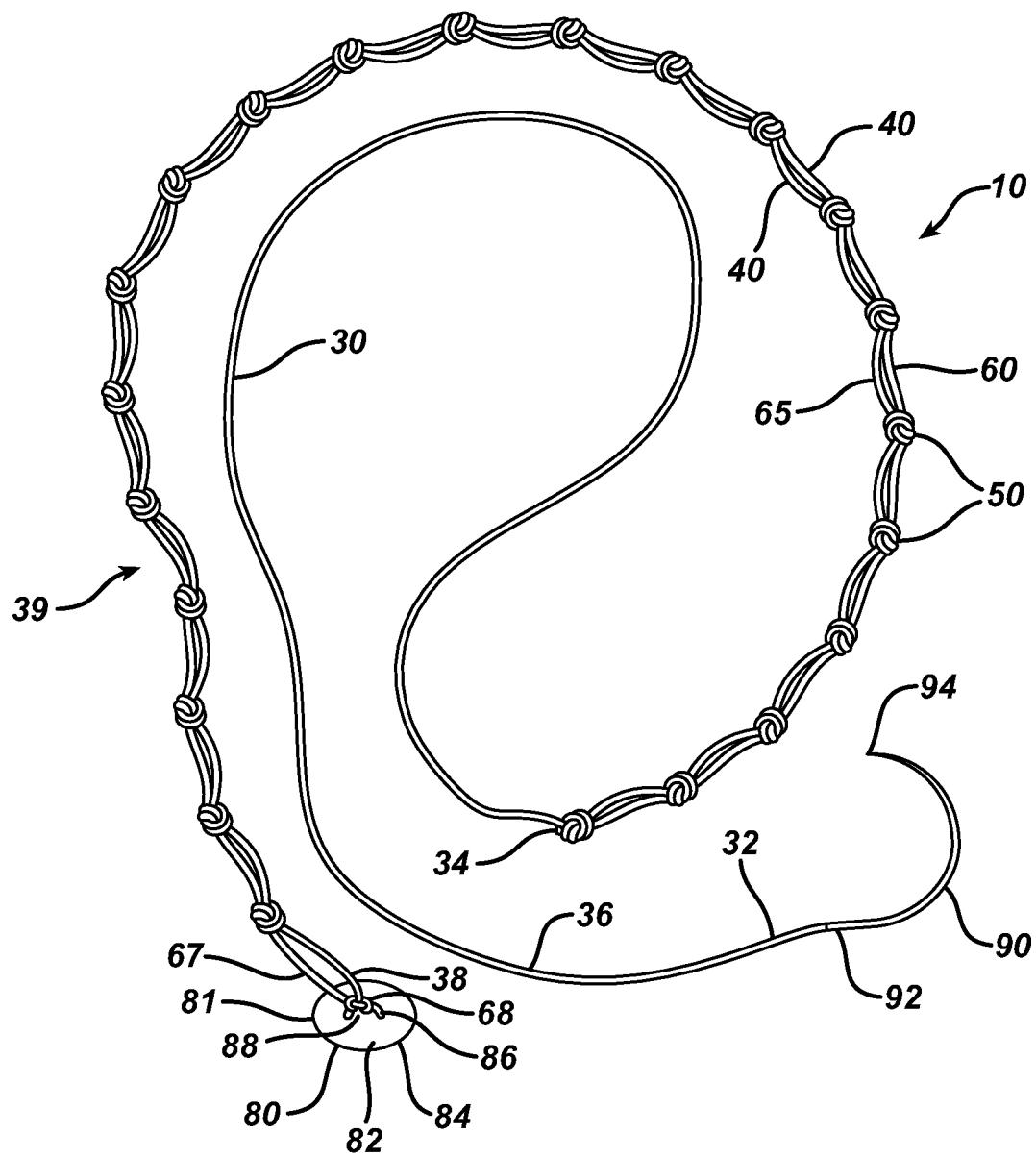
FIG. 1 is a perspective view of a knotted suture of the present invention, wherein the suture is a monofilament suture.

The term interrupted stitch as used herein is defined to have its conventional meaning, and can be described in the following manner. An interrupted stitch is a suture line that uses a number of suture strands to close the wound. Each strand is tied and cut after insertion.

The term cross stitch as used herein is defined to have its conventional meaning, and can be described in the following manner. A cross stitch is a suture line that uses a number of suture strands to close the wound. Each strand passes through the tissue twice and the suture is locked and cut. The resulting stitch is a cross-type stitch. The term cross stitch is also used interchangeably with the synonymous termscross mattress suture, X-mattress suture and cruciate suture.

The sutures that can be used to make the knotted suture devices of the present invention include conventional monofilament and braided sutures. The sutures can be made from conventional non-absorbable materials, including polyesters, polypropylene, polyethylene, silk, Nylon, and the like and equivalents thereof. The sutures can also be made from conventional bioabsorbable or biodegradable polymeric materials including polydioxanone, polylactic acid,poly(lactic-co-glycolic acid), polycaprolactone, catgut, copolymers, and the like and equivalents thereof. The sutures may have a variety of conventional suture sizes ranging from 8-0 to 2.

The sutures used to make the knotted suture devices may also have conventional coatings including lubricious coatings such as silicones, beeswax, and paraffin. The coatings may also be made from bioabsorbable or nonabsorbable polymers such as polybutylate, Teflon, Polyglactin 370, polycaprolate, and poly(oxyethylene-oxypropylene. The coatings may additionally contain conventional therapeutic agents such as antibiotics, antimicrobial agents (e.g. silver, Diiodomethyl-p-tolylsulfone, 2,4,4'-Trichloro-2'-Hydroxydiphenyl Ether or combination thereof) and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, radioactive agents, osteoinductive agents, cystostatics heparin neutralizers, procoagulants and hemostatic agents, such as prothrombin, thrombin, fibrinogen, fibrin, fibronectin, heparinase, Factor X/Xa, Factor VII-NIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents and synthetic peptides having hemostatic activity.

The knotted suture devices according to the present invention may further comprise conventional coatings and equivalents thereof on the surfaces to improve lubricity, durability and therapeutic functionality. Such coatings can be applied by dipping, spraying, wiping or rolling onto the suture surface. Further, the suture surface can be treated, for example with an oxygen plasma, prior to its coating to enhance the coating's durability. Materials used for the coatings may include, without limitation, silicones, beeswax, paraffin, polybutylate, Teflon, Polyglactin 370, polycaprolate, and poly(oxyethylene-oxypropylene). In a non-limiting exemplary embodiment, the coating consists of a silicone polymer, a silicone cross-linking agent, a catalyst, a slip agent and a compatible solvent.

The anchor members used with the knotted suture devices of the present invention are made from conventional biocompatible materials. "Biocompatible" as used herein refers to a material that, once implanted, does not interfere significantly with wound healing and/or tissue regeneration, and does not cause any significant metabolic disturbance. "Biodegradable" and "bioabsorbable" as used herein refer to a material that is broken down spontaneously and/or by the mammalian body into components, which are consumed or eliminated in such a manner as not to interfere significantly with wound healing and/or tissue regeneration, and without causing any significant metabolic disturbance.

Suitable nonabsorbable polymers include, but are not limited to acrylics, polyamide-imide (PAI), polyarcryletherketones (PEEK), polycarbonate, polyethylenes (PE), polybutylene terephthalates (PBT) and polyethylene (PET), terephthalates, polypropylene, polyamide (PA), polyvinylidene fluoride (PVDF), and polyvinylidene fluoride,-cohexafluoropropylene (PVDF/HFP), polymethylmetacrylate (PMMA) and combinations thereof.

Suitable absorbable polymers may be synthetic or natural polymer. Suitable biocompatible, bioabsorbable polymers include polymers selected from the group consisting of aliphatic polyesters, poly (amino acids), copoly (ether-esters), polyalkylenes oxalates, polyamides, tyrosine derived polycarbonates, poly (iminocarbonates), polyorthoesters, polyoxaesters, polyamidoesters, polyoxaesters containing amine groups, poly (anhydrides), polyphosphazenes, and combinations thereof. For the purpose of this invention aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof. Natural polymers include collagen, elastin, hyaluronic acid, laminin, and gelatin, keratin, chondroitin sulfate and decellularized tissue.

Suitable metals are those used conventionally in medical devices including, but not limited to titanium, titanium alloys, tantalum, tantalum alloys, stainless steel, and cobalt-chromium alloys (e.g., cobalt-chromium-molybdenum alloy) and the like. These metals are conventionally used in sutures, orthopedic implants, wound staples, vascular staples heart valves, plastic surgery implants and the like.

Suitable absorbable or biocompatible glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

The suture devices of the present invention may be mounted to the suture mounting ends of conventional surgical needles by using conventional mounting techniques such as mechanical swaging, gluing, cementing, heat shrink tubing, etc. The surgical needles useful with the knotted suture devices of the present invention may be made from conventional materials such as surgical stainless steels, high strength metal alloys, high modulus metal alloys, refractory metal alloys and the like and equivalents thereof.

Referring now to FIG. 1, a knotted suture device 10 of the present invention is seen. The device 10 has a suture strand 30. Strand 30 is a monofilament suture. Suture strand 30 is seen to have first end 32 and second end 34. In addition, strand 30 has extending section 36 adjacent to second end 32. The end 32 is mounted to surgical needle 90. Surgical needle 90 is seen to have proximal suture mounting end 92 and distal piercing point 94. End 32 of suture strand 30 is seen to be mounted in suture mounting end 92 of surgical needle 90, while end 34 is free. The device 10 is seen to have a plurality of loop sections 60 formed by knots 50 in suture section 39. The loops 60 and knots 50 form suture section 39 in suture strand 30. Loop sections 60 are seen to have openings 65 between suture sections 40 that form the loop sections 60. Each loop section 60 is seen to be bounded by knots 50 and suture sections 40, except for the last loop section 60 which is identified as loop section 67, and which only has one knot 50. Knots 50 are conventional knots, including square knots, surgeon's knots, etc. As illustrated in FIG. 1, the knot 50 is a surgeon's knot. Mounted to the loop section 67 is the anchor member 80. As illustrated, anchor member 80 is seen to have disc member 81, which has a preferably flat configuration. The disc member 81 is seen to have top 82 and bottom 84. The anchor member 80 is also seen to have suture mounting member 86 extending thorough and from top 82. Member 86 is seen to be a curved member creating suture opening 88. The member 86 also has section 87 that extends back through disc 81 adjacent to bottom 84 to provide a looped member that can be constructed for example from suture. If desired, member 86 may be a curved member that extends only from top 82 and that does not extend back through member 81 to bottom 84. A conventional knot 68 affixes or mounts anchor member 80 to loop section 67 via suture mounting member 86 and opening 88, e.g., square knot, surgeon's knot, etc. Although not preferred, the anchor member 80 may be mounted to loop section 67 without a knot so that it is moveable or slideable about section 67. The loop sections 60 are formed in the following manner. The suture 30 is doubled over itself in a manner such that end 32 extends for a desired distance beyond end 34, and such that the suture 30 has a bottom looped suture segment 38 that forms loop section 67. Anchor member 80 is mounted to the suture 30 and located at the bottom suture section 38 (loop section 67), and an appropriate optional knot 68 is tied. Next, the knots 50 are emplaced in the suture 30 in the following manner. After the anchor member 80 has been mounted as described above, and the length of strand 30 is adjusted to provide for a desired extended section 36.

The two sections of the strand 30 are knotted to form the loop sections 60 and the knots 50 using the conventional knots described above. The length of a loop 60 is determined by the distance of the adjacent two knots 50, which can be varied according to the need, typically from 2 mm to 15 mm. Although it is preferred that the loops 60 have equal lengths, it is also within the scope of the present invention to have one or more loops 60 having varying length.

Figure 2:
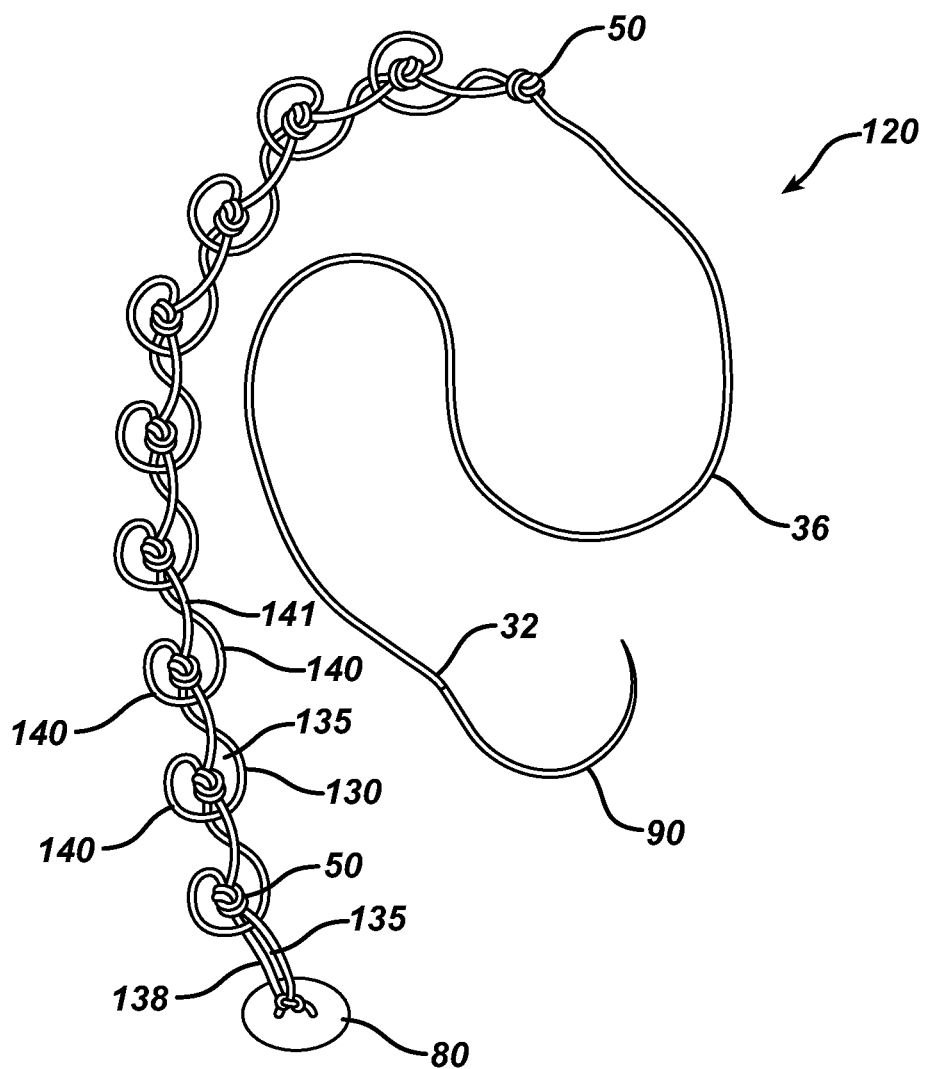
FIG. 2 is a perspective view of an alternative embodiment of a monofilament knotted suture of the present invention having a different loop configuration.

FIGS. 2-5 illustrate alternate embodiments of the knotted suture device of FIG. 1. Accordingly, common features of the devices will bear common reference numerals. FIG. 2 illustrates an embodiment of a knotted suture device 120 of the present invention having a different loop configuration. The device 120 differs from device 10 in that each loop section 130 has a strand of suture section 140 passing through each opening 135 of each loop section 130. The device also has a bottom loop section 138, which also has opening 135. Each loop section 130 has first suture section 140 and second suture section 141. First loop section 140 is longer than second loop section 141 and is threaded back into the opening 135 of the adjacent loop 130. The advantage of this configuration is the insertion of the anchor member 80 in an opening 135 may be facilitated due to the increased size of the opening 135 of the loop 130. The knots 50 are emplaced in a similar manner to that of device 10. The surgical needle 90 is mounted to strand 30 in a conventional manner, such as swaging.

Figure 3:
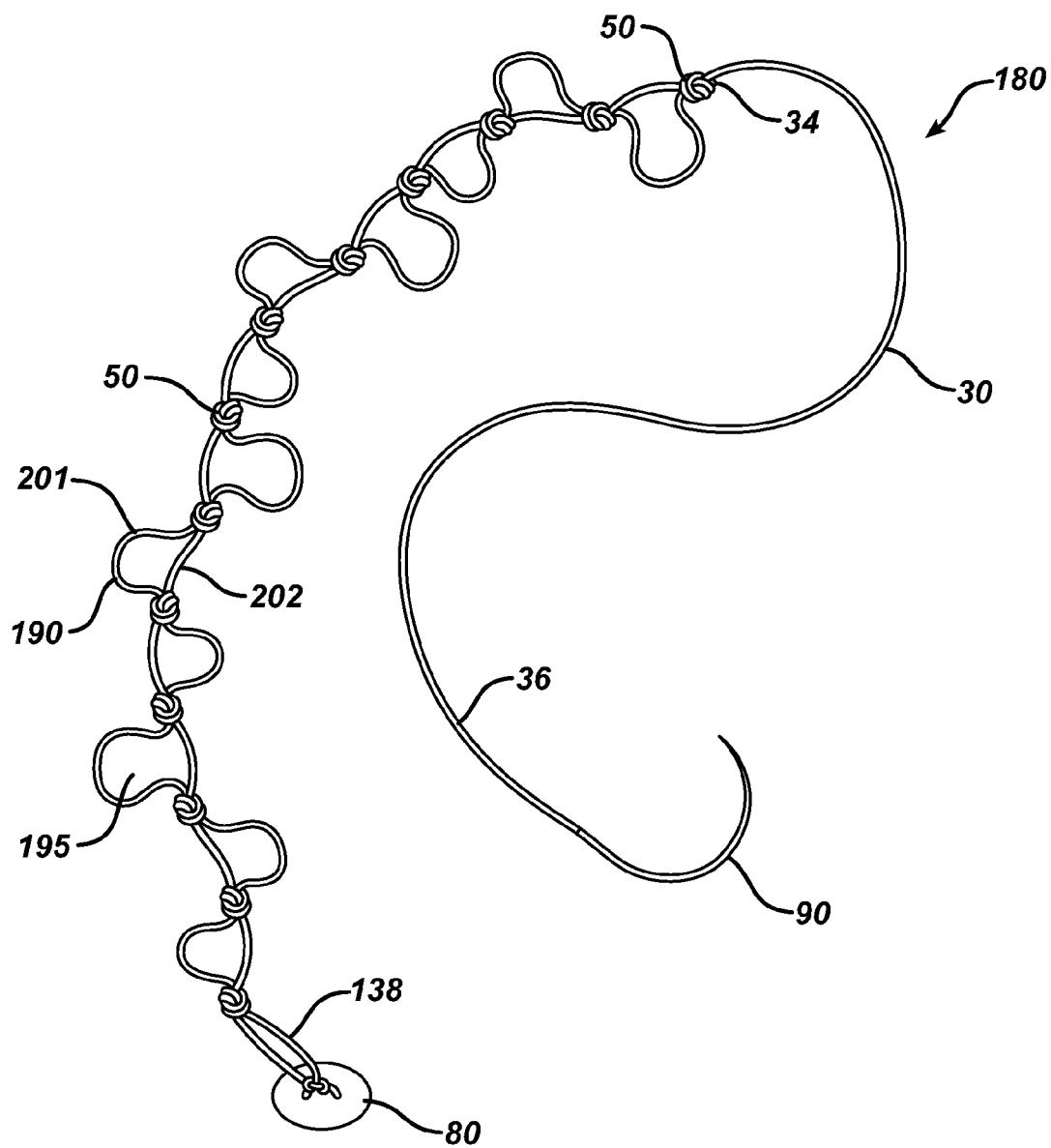
FIG. 3 is a perspective view of another alternate embodiment of a monofilament knotted suture of the present invention having another different loop configuration.

FIG. 3 illustrates yet another embodiment of a knotted suture device 180 of the present invention having a different loop structure. The device 180 differs from device 10 in that the loop structures 190 have one suture strand section 201 that is larger on one side of opening 195 than the opposed section 202. The advantage of this configuration is the insertion of the anchor member 80 into openings 195 may be facilitated. The knots 50 are emplaced a manner as described above, and the needle 90 is mounted to suture 30 in a conventional manner such as by mechanical swaging. If desired, the loops 190 may be arranged in a sinusoidal configuration.

Figure 4:
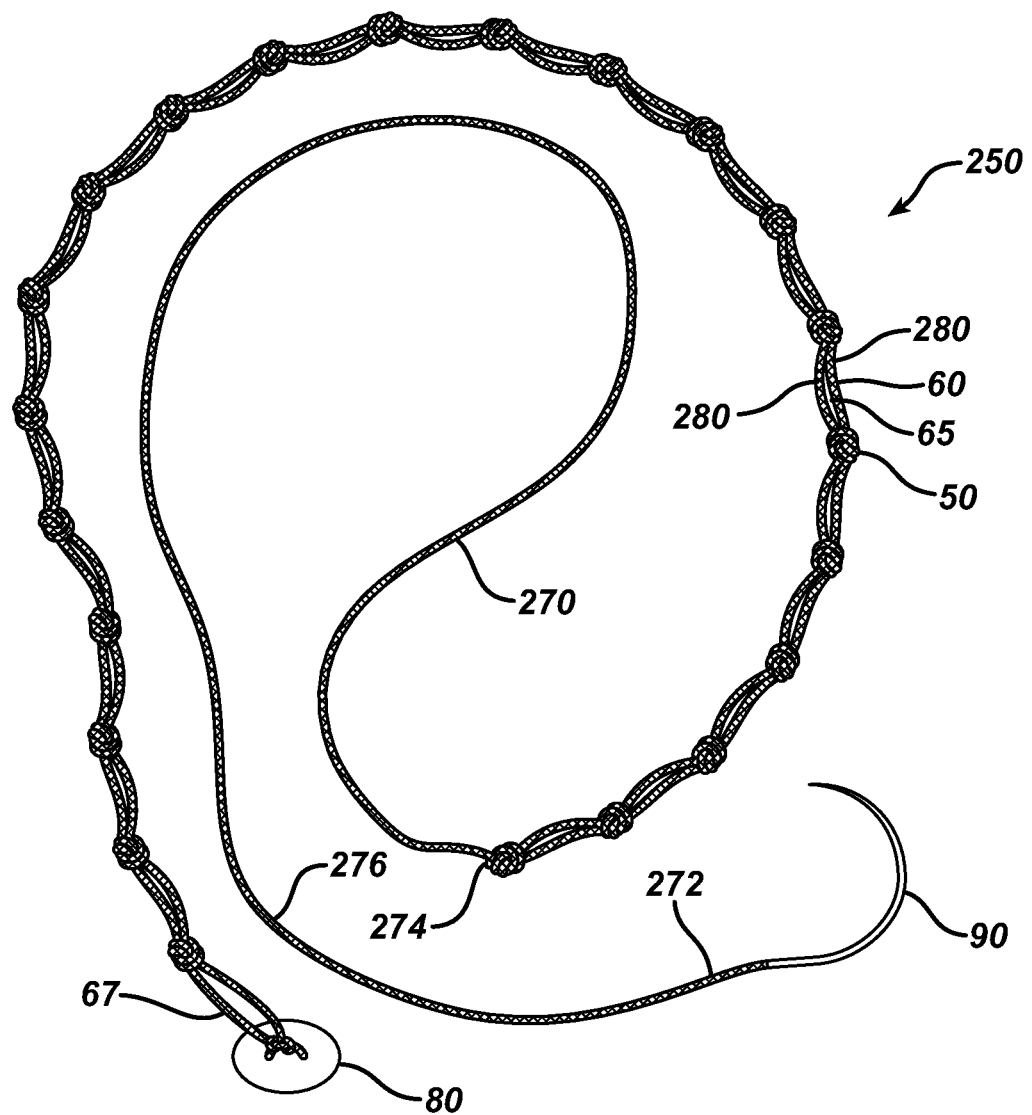
FIG. 4 is a perspective view of a knotted suture of the present invention having a structure similar to the suture of FIG. 1, but wherein the suture is a braided suture.

Referring now to FIG. 4, an alternate embodiment of the device 10 of FIG. 1 is seen. The device 250 is otherwise identical to device 10 except that monofilament suture 30 has been replaced by braided suture 270. Device 250 is similarly seen to have loop sections 60 having openings 65. The sections 60 have opposed suture sections 280 separated by knots 50. Device 250 is also seen to have bottom loop section 67 and anchor member 80. The suture 270 is seen to have first end 272, second end 274 and leading section 276. Device 250 is made in a manner similar to device 10 as described above.

Figure 5:
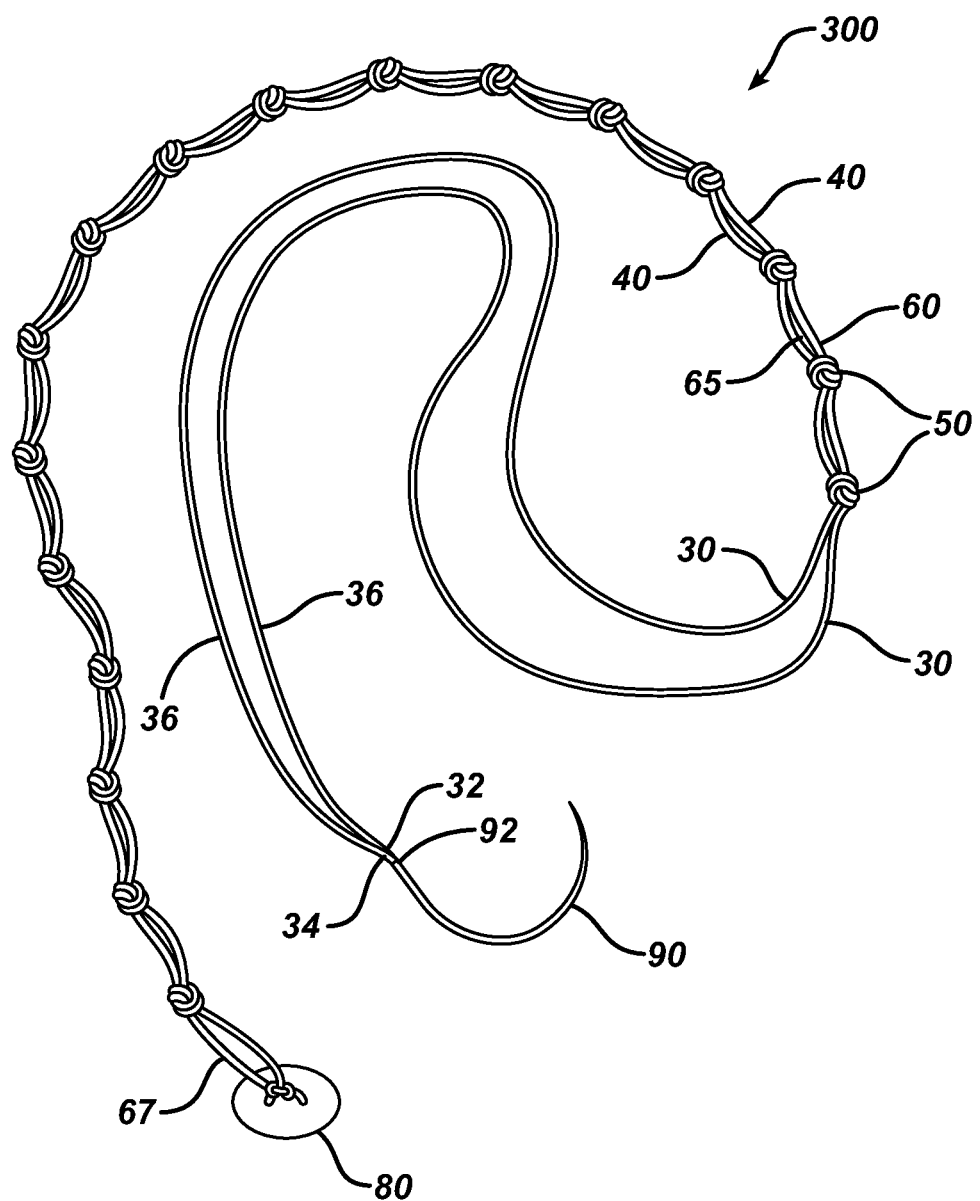
FIG. 5 is a perspective view of a knotted suture of the present invention wherein both ends of the suture are mounted to a surgical needle.

Illustrated in FIG. 5 is an embodiment of a suture device 300 of the present invention that is similar to device 10, but has two extending sections 36. In addition, both the first end 32 and second end 34 of suture strand 30 are mounted to the proximal suture mounting end 92 of surgical needle 90.

Figure 6:
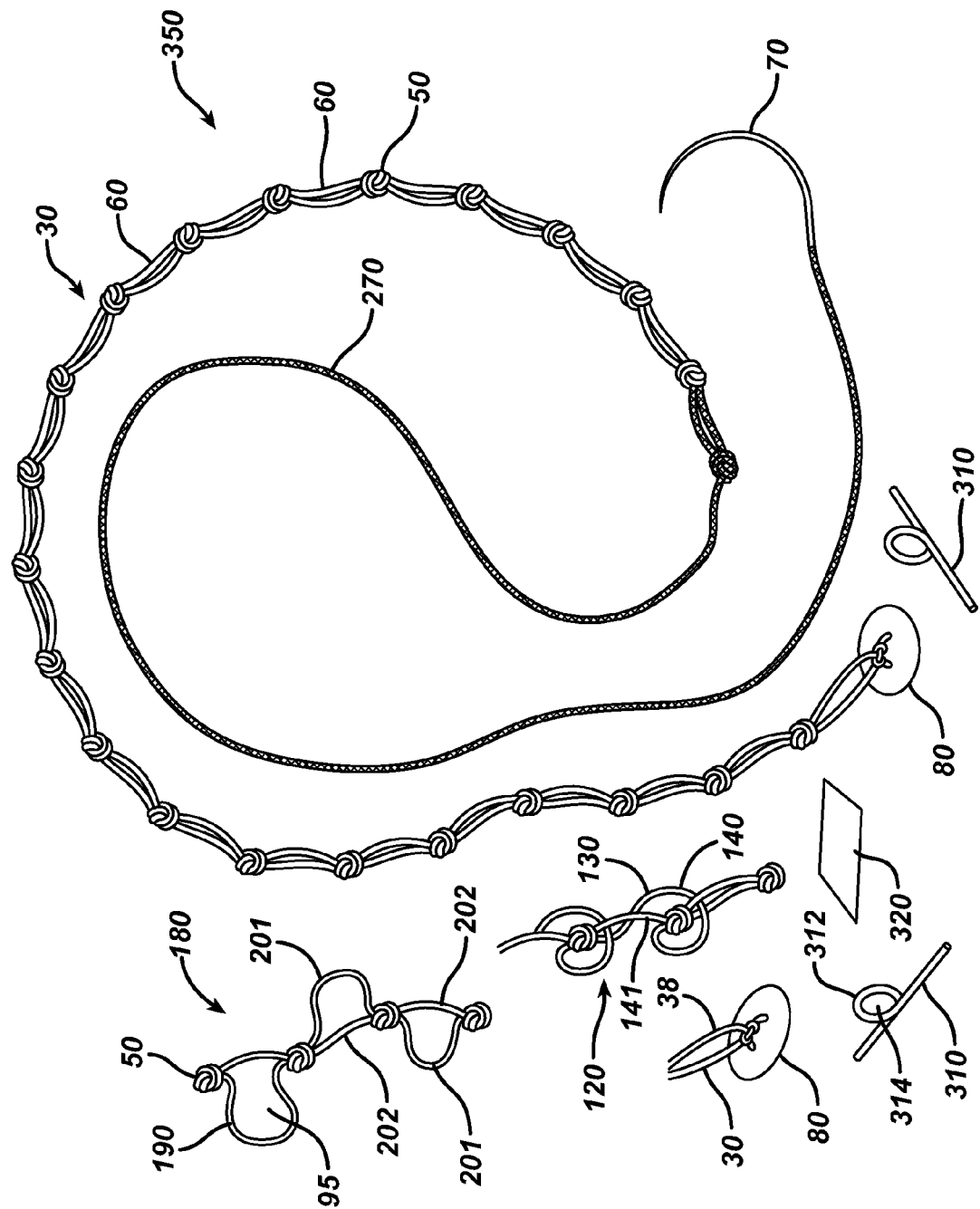
FIG. 6 is a perspective view of a knotted suture of the present invention showing a combination of all of the features of FIGS. 1-5 for illustration purposes, as well as showing various embodiments of an anchor member.
Figure 7:
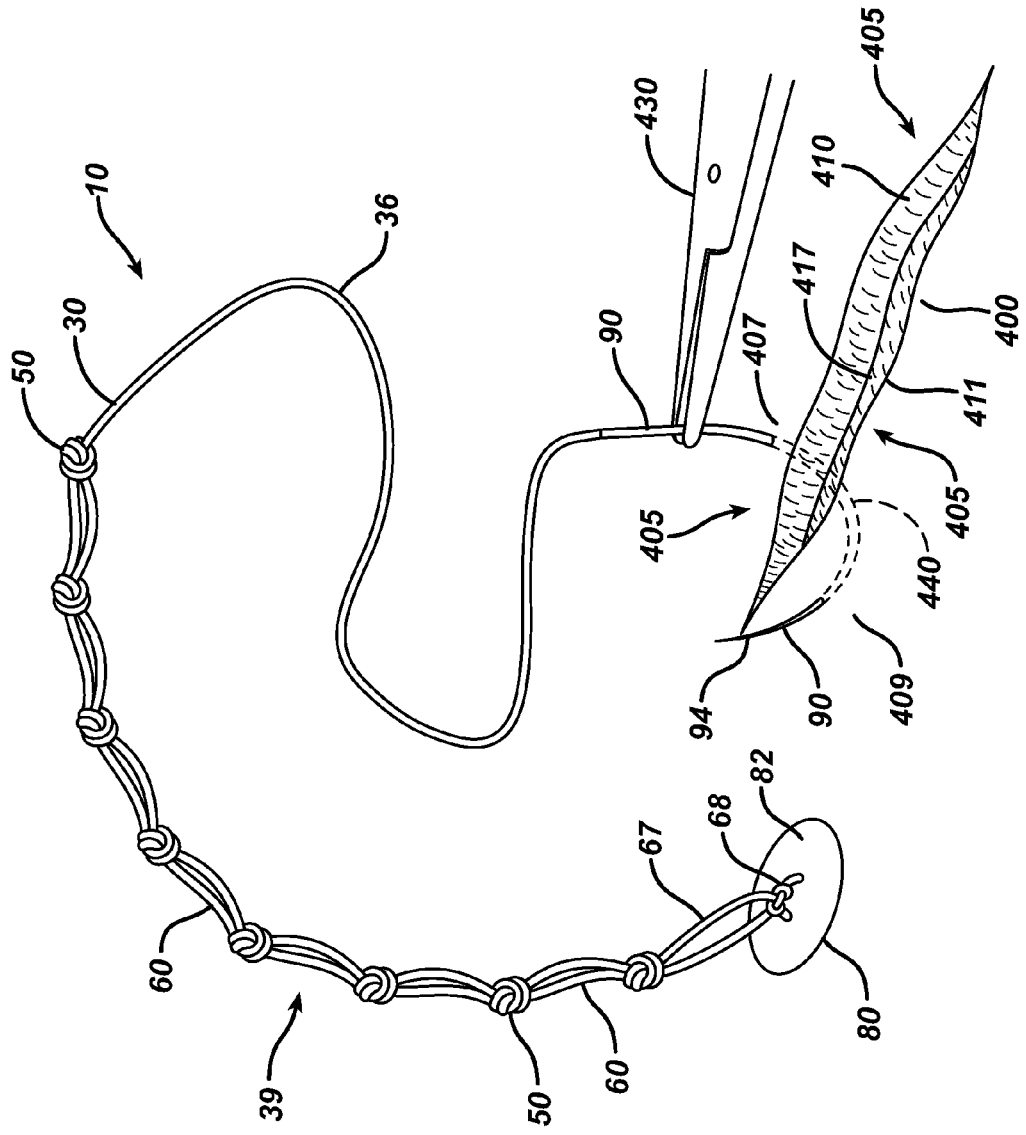
FIGS. 7-13 illustrate perspective views of a surgical procedure using the suture device of FIG. 1 to approximate tissue using an interrupted stitch.
Figure 8:
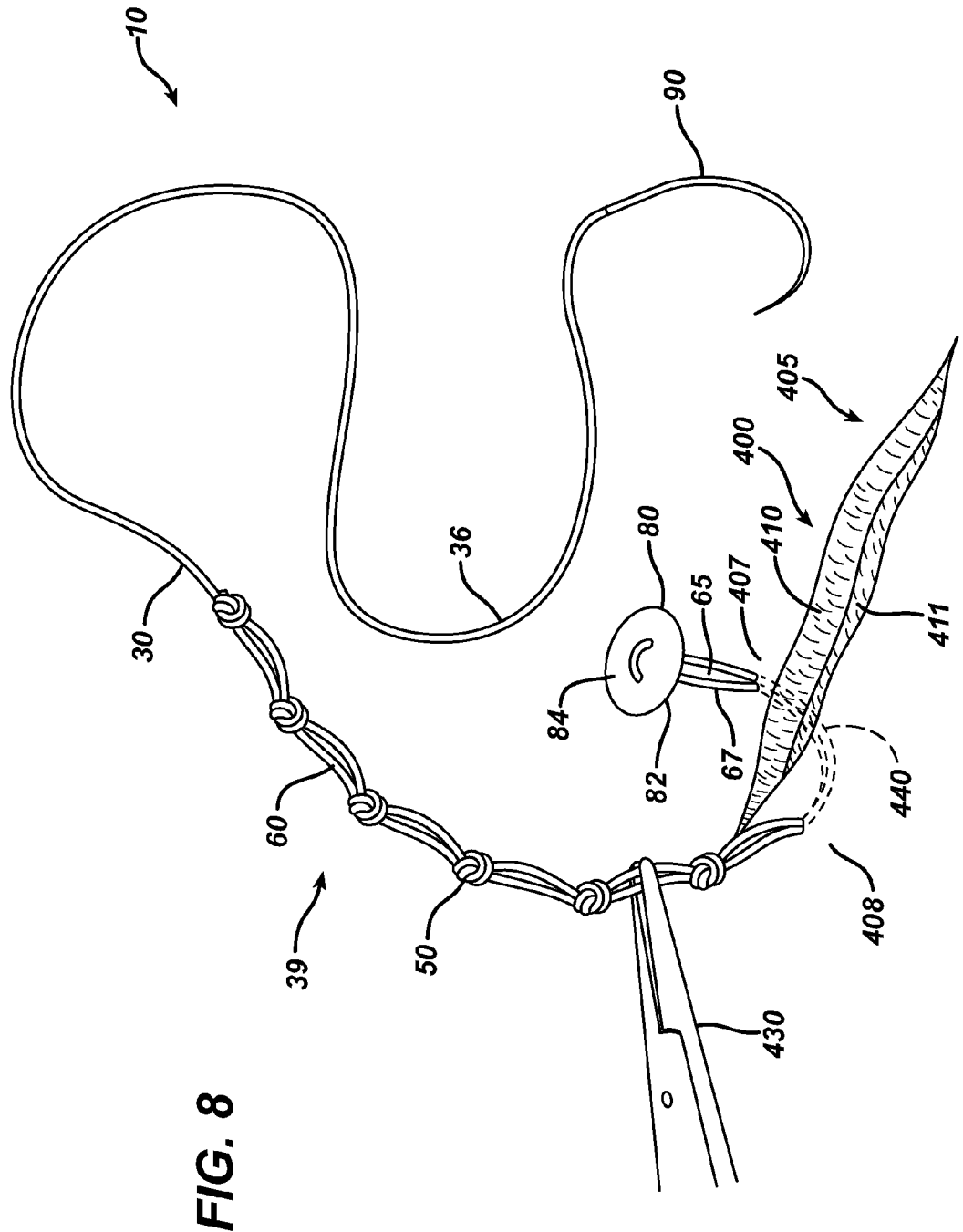
Figure 9:
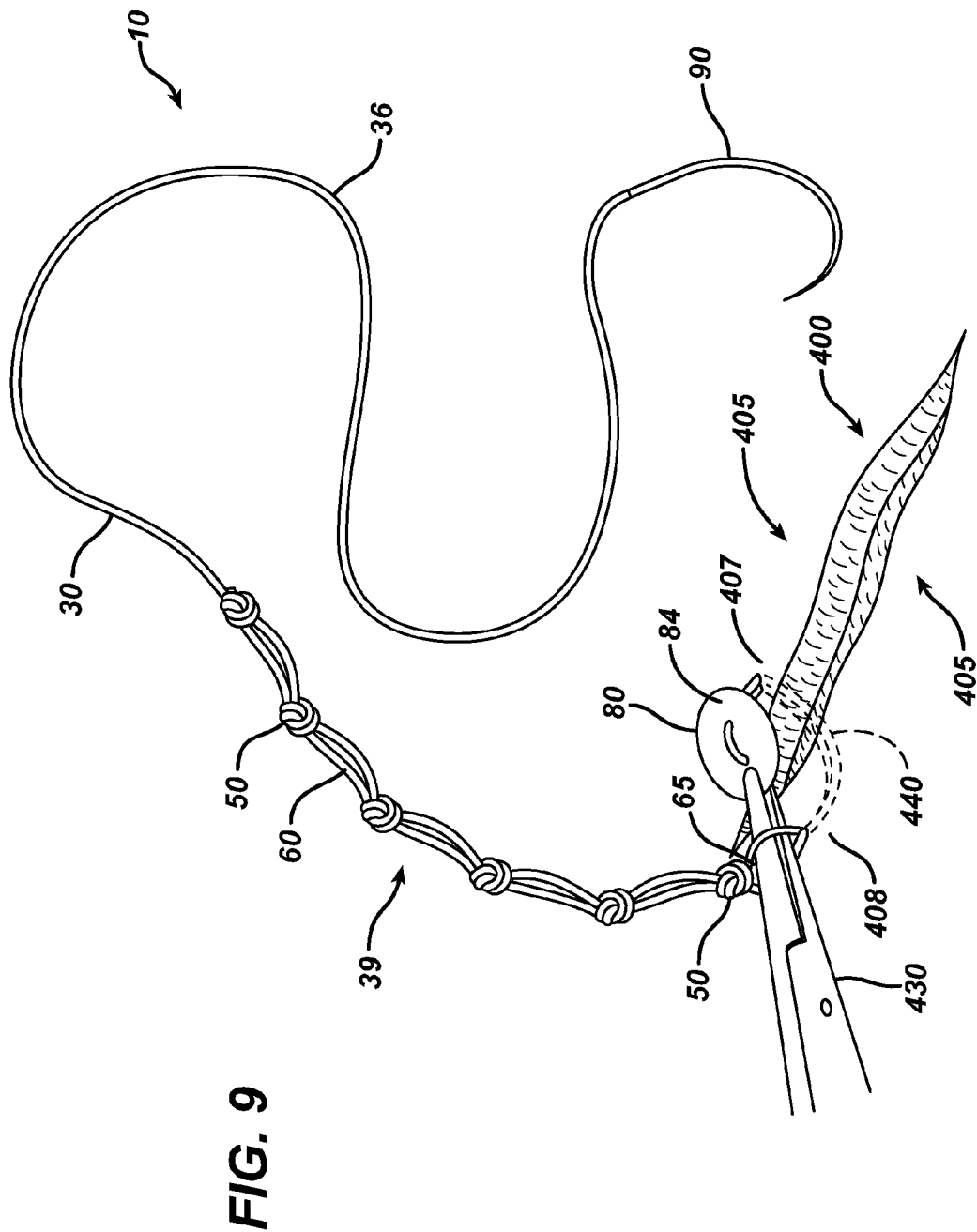
Figure 10:
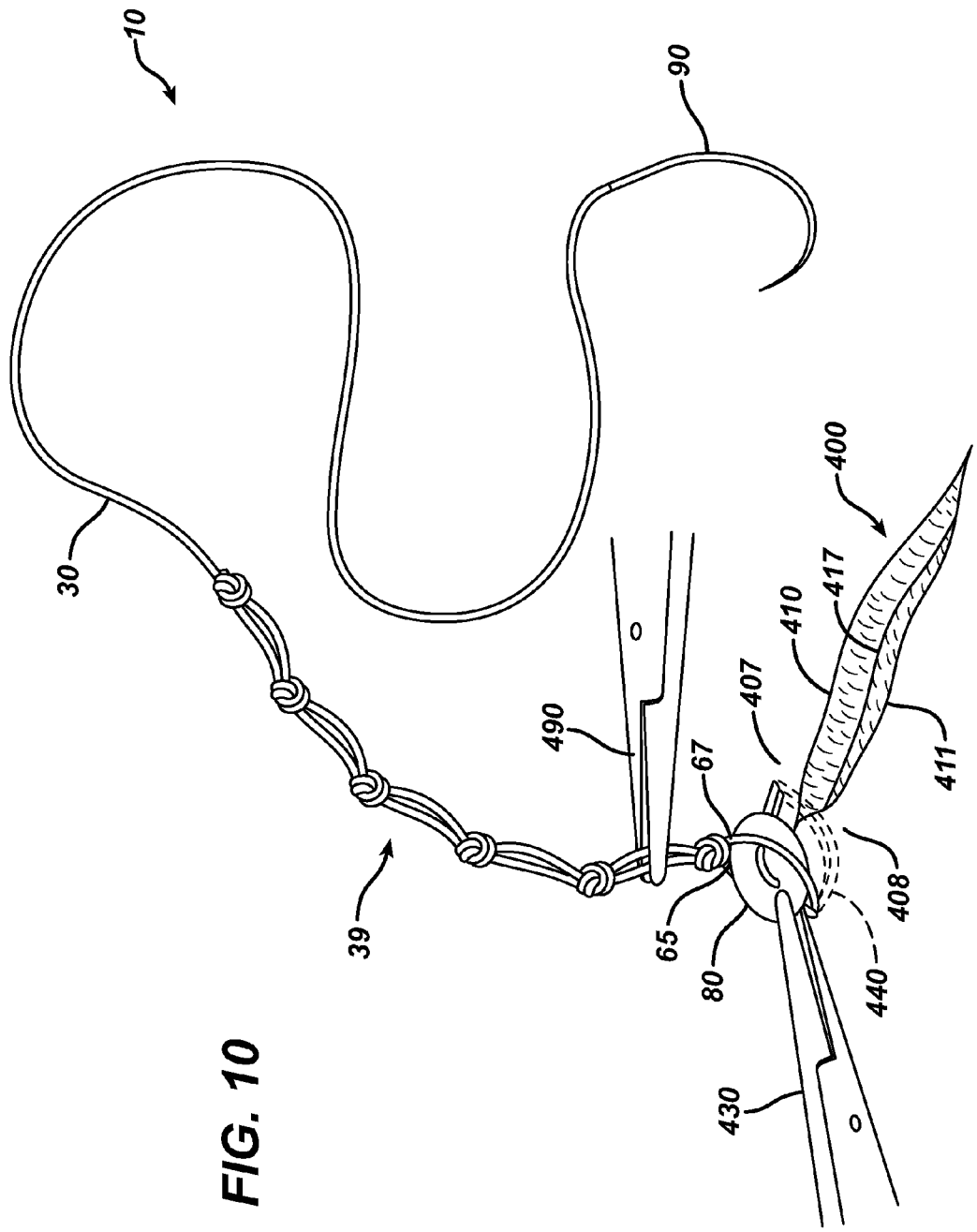
Figure 11:
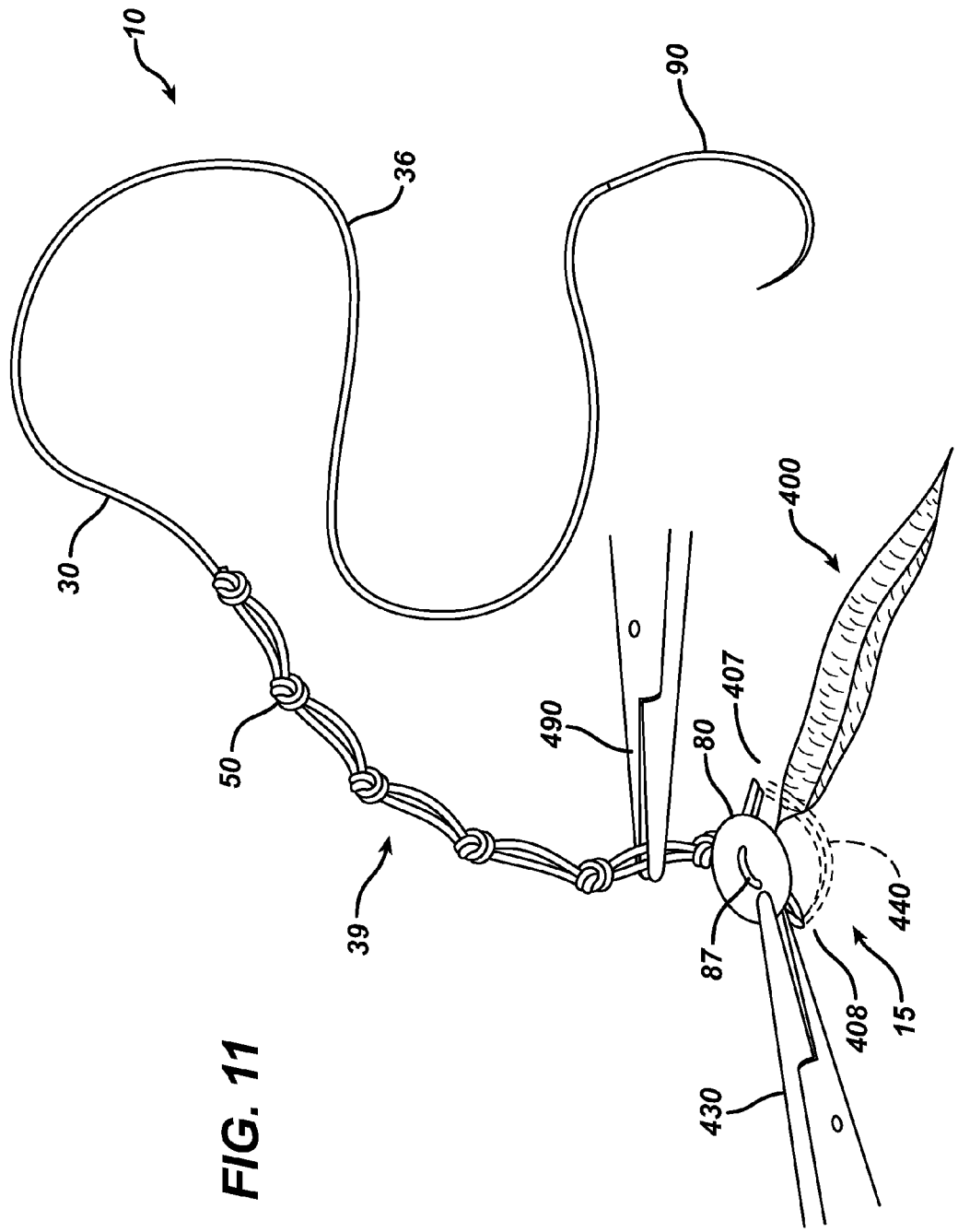
Figure 12:
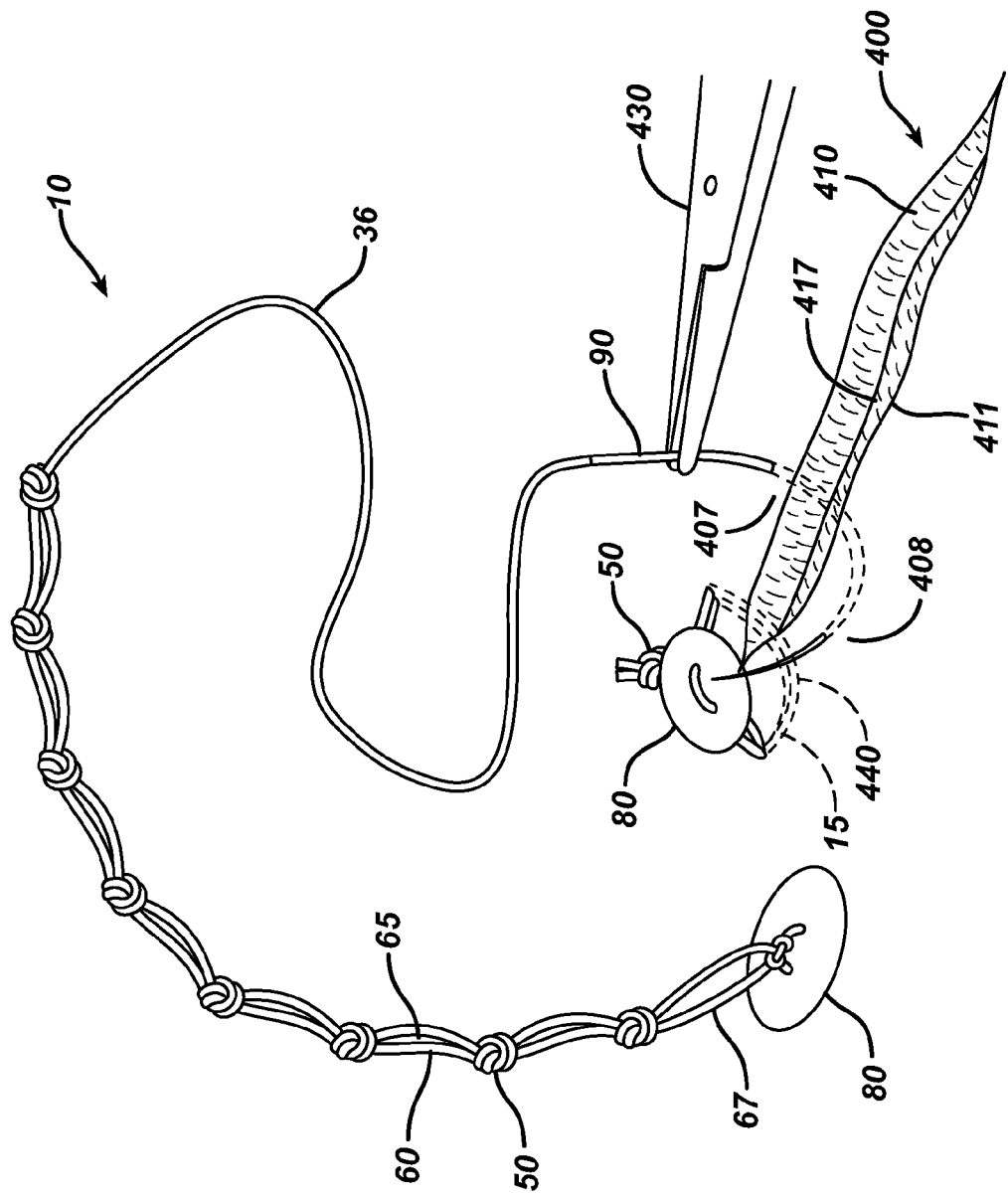
Figure 13:
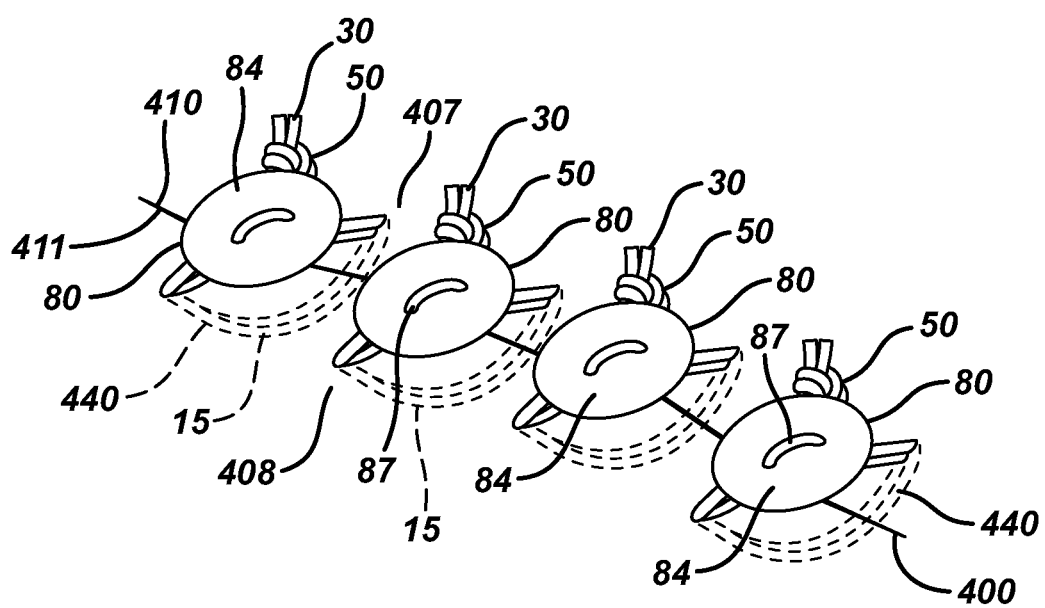
Figure 14:
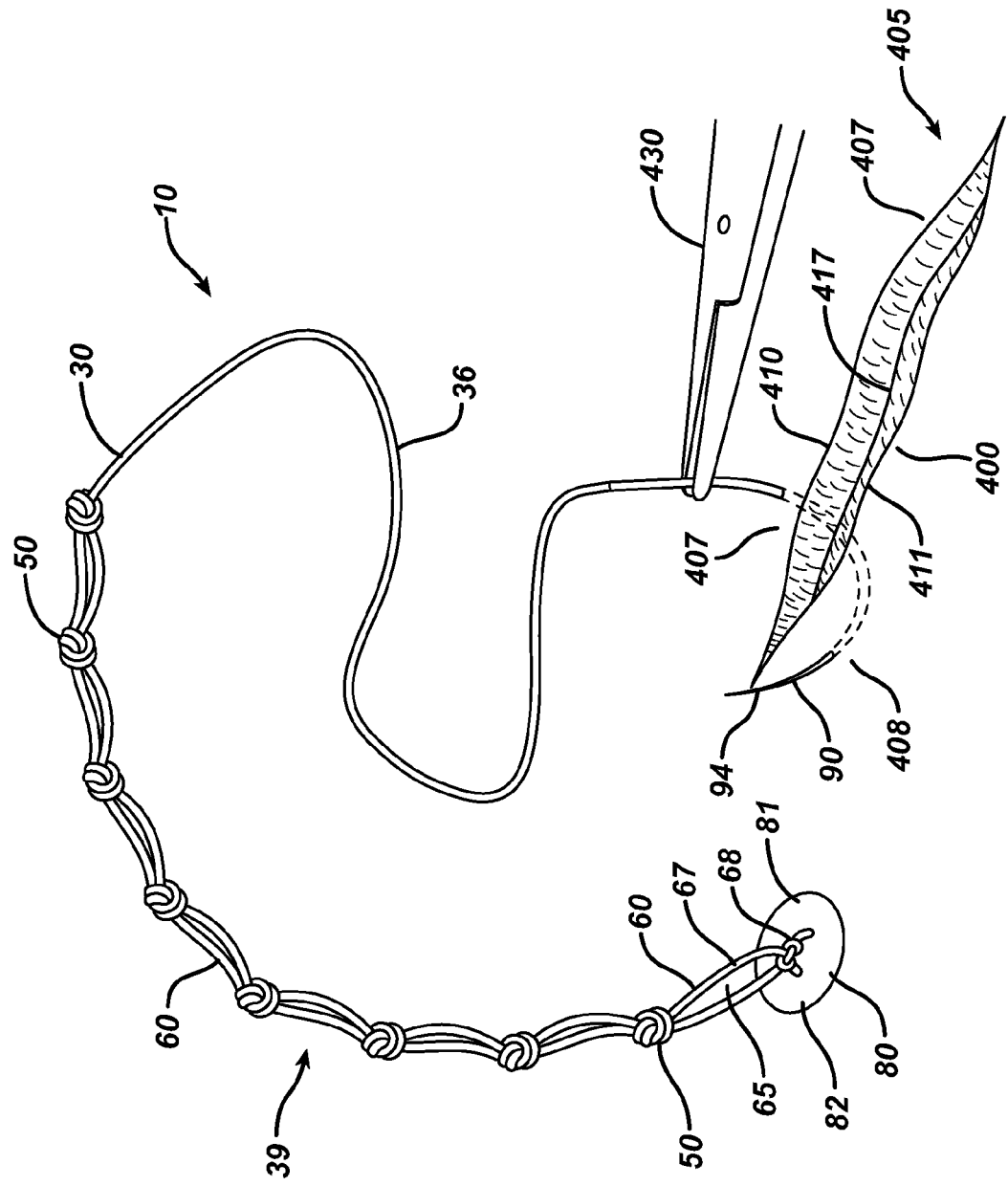
FIGS. 14-19 illustrate perspective views of a surgical procedure using the suture device of FIG. 1 to approximate tissue using a cross stitch.
Figure 15:
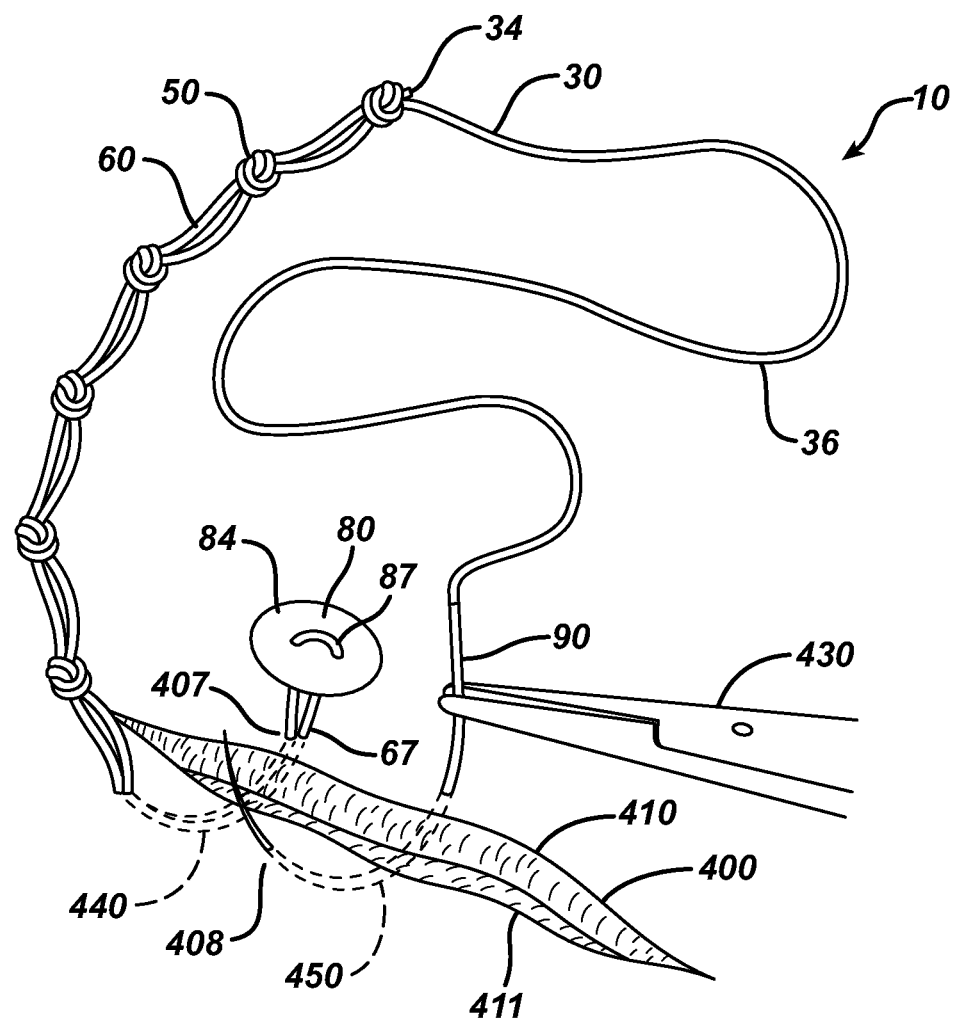
Figure 16:
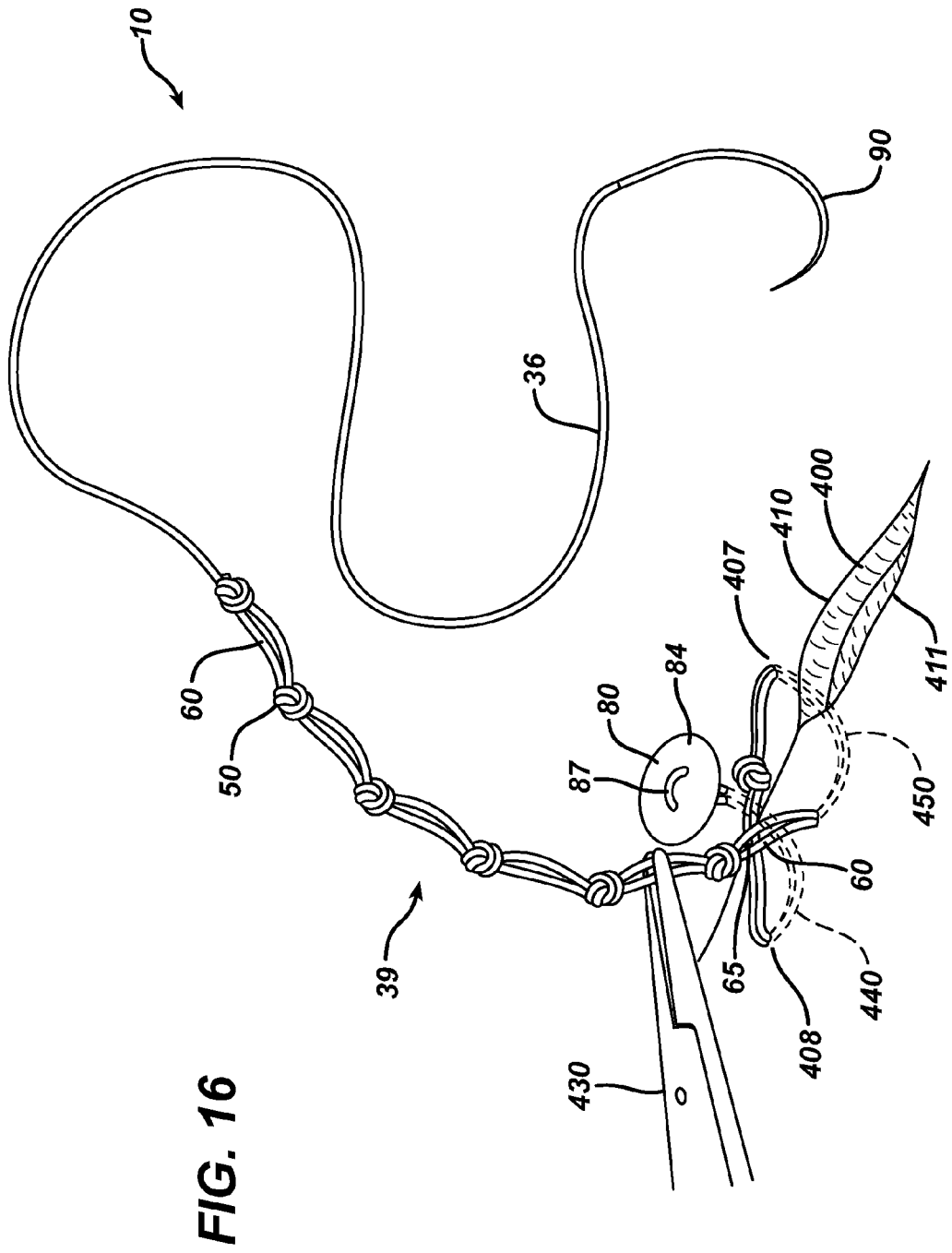
Figure 17:
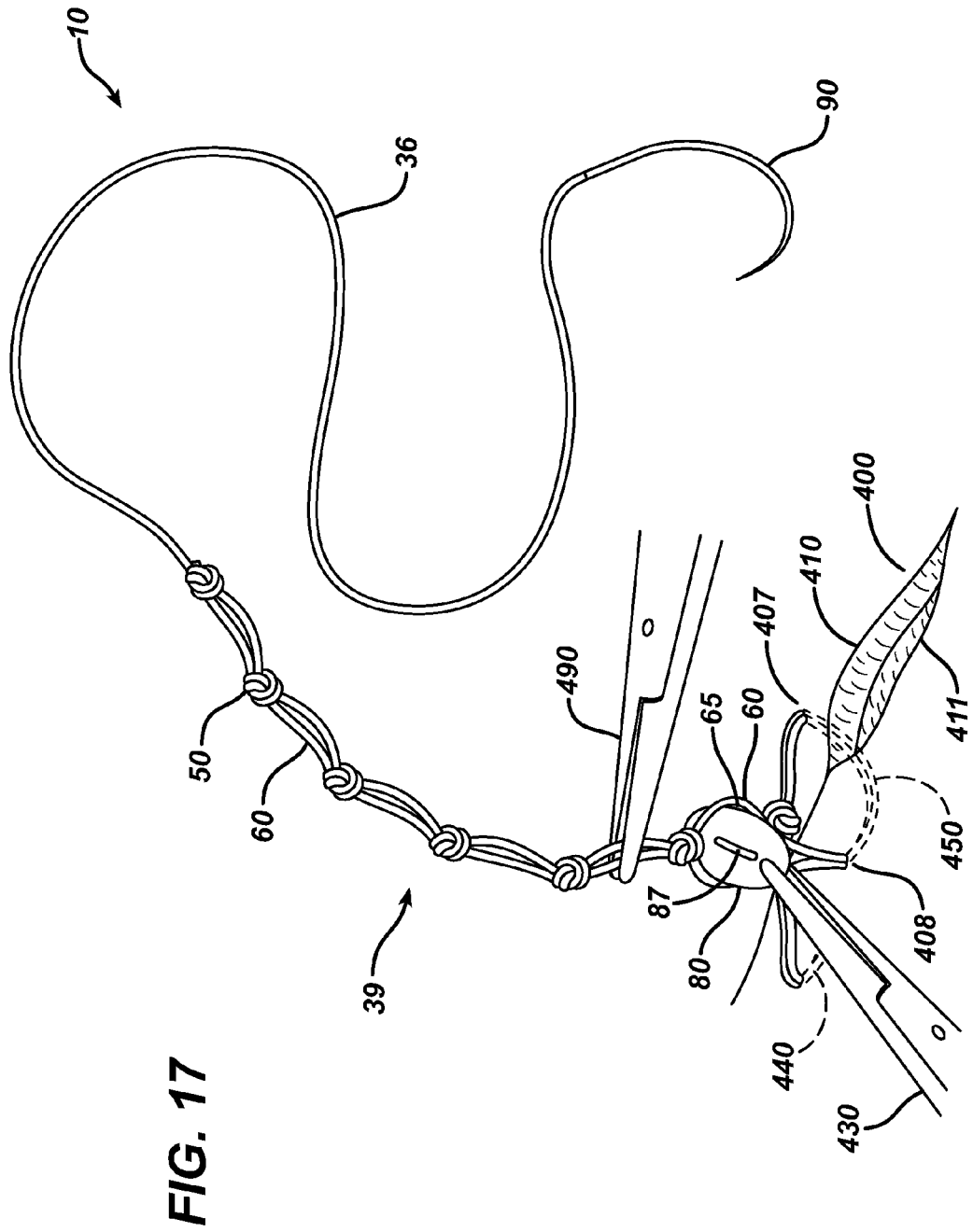
Figure 18:
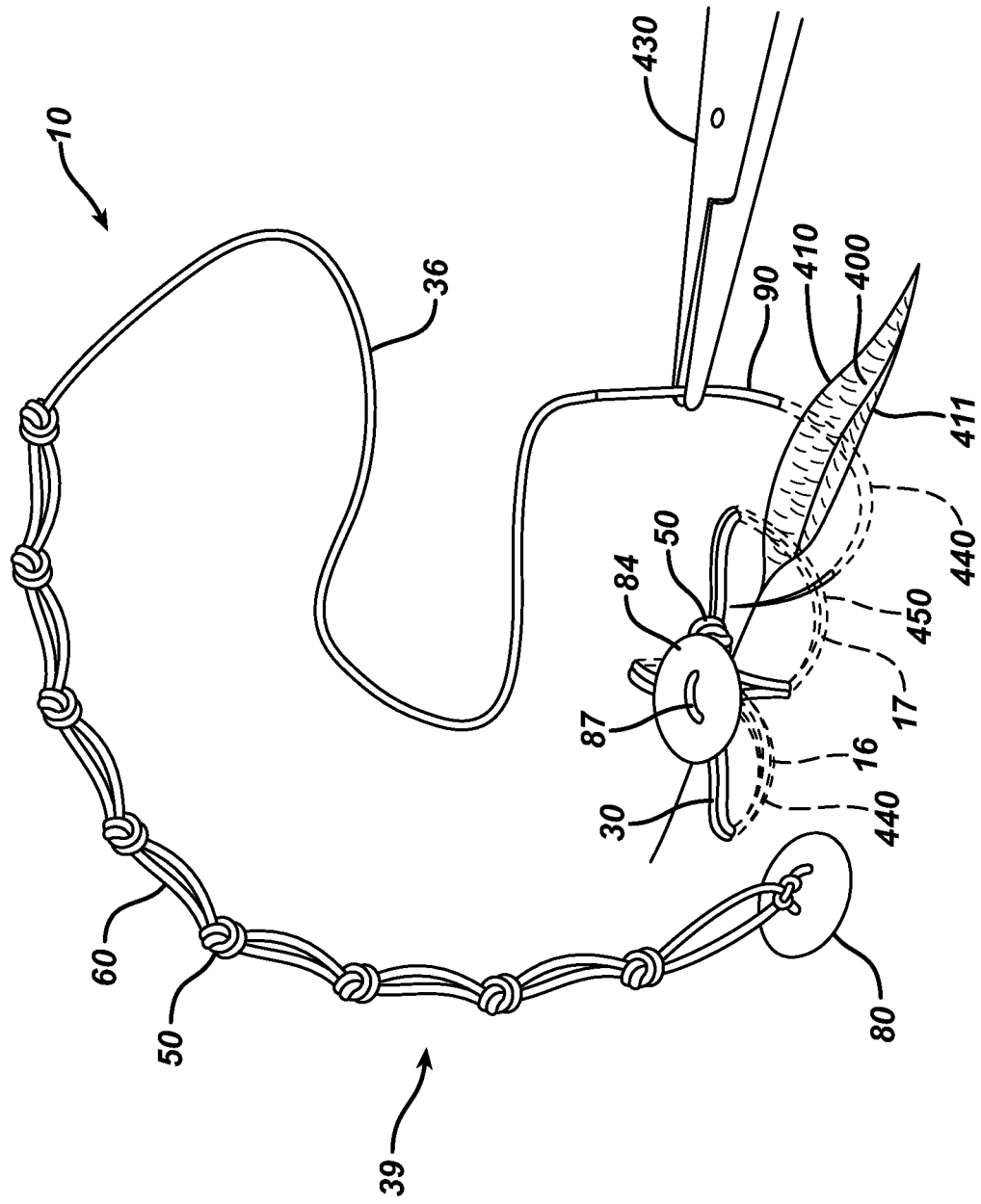

As seen in FIG. 6, a surgical suture device 350 of the present invention is shown presented as a composite of several various embodiments previously described for illustrative purposes. The illustrative device 350 has knots 50, loops 60 and surgical needle 90 as well as anchor member 80. Also illustrated are partial sections of device 120 and device 180 illustrating loop sections 130 and 190, respectively. Also seen in FIG. 6 are alternate embodiments of anchor member 80. Anchor member 310 is seen to be an elongated rod twisted to form a suture mounting loop 312 having opening 314. Anchor member 320 is seen to be a substantially flat rectangular member. The anchor member 320 is mounted to the end loop of a device of the present invention in any conventional manner, for example by having openings in the member 320 through which stand section 38 is threaded and optionally knotted.

A surgical procedure utilizing a knotted suture device 10 of the present invention to approximate tissue surrounding a wound 400 is illustrated in FIGS. 7-13. The procedure utilizes an interrupted stitch. In the initial step, the surgeon grasps needle 90 using a conventional needle holder instrument. The surgeon rotates the needle such that the piercing distal end 94 of the needle penetrates tissue 405 having top surface 407 adjacent to side 410 of wound 400 and then pushes the needle 90 until the distal end 94 exits tissue 405 through surface 409 adjacent to opposed side 411 of wound 400 and so that the needle passes below the bottom 417 of wound 400 thereby creating a tissue pathway 440 for suture strand 30. Although not shown, the needle 90 may be passed though the tissue surrounding the wound 400 such that it does not pass below bottom 417, but passes above bottom 417 through sides 410 and 411. As seen in FIGS. 8-13, the surgeon has pulled the needle 90 through the tissue 405 and the top side 82 of anchor member 80 is adjacent to wound side 410 on surface 407. The surgeon then inserts the needle holder 430 through an opening 65 in a loop section 60 (in this case end loop 67) and grasps anchor member 80 and pulls it through the opening 65. The surgeon uses an optional second holder or grasper instrument 490 to pull on suture strand 30 and provide tension. This secures a section of the suture filament 30 about the wound 400, and locks the suture thereby approximating a section of wound sides 410 and 415 thereby forming a stitch 15 without requiring a surgical knot to secure the suture. The excess suture strand 30 with attached needle 90 is then cut adjacent to a knot 50 as illustrated. The process is repeated with three additional devices 10 to complete the approximation of the sides 410 and 411 of wound 400 with interrupted stitches 15. Although the use of two needle holder and grasper instruments is illustrated, the procedure may be completed using a single holder or grasper. It will also be appreciated by those skilled in this art that similar grasping or manipulating instruments may be used to emplace the devices 10 of the present invention, preferably those designed for minimally invasive procedures. It should also be noted that depending upon the surgical procedure and the nature of the wound to be closed as well as the type of tissue to be approximated and the suture pathway, the anchor member 80 may be passed through a loop 60 that is not the end loop 67 in order to lock the suture stitch in place.

Figure 19:
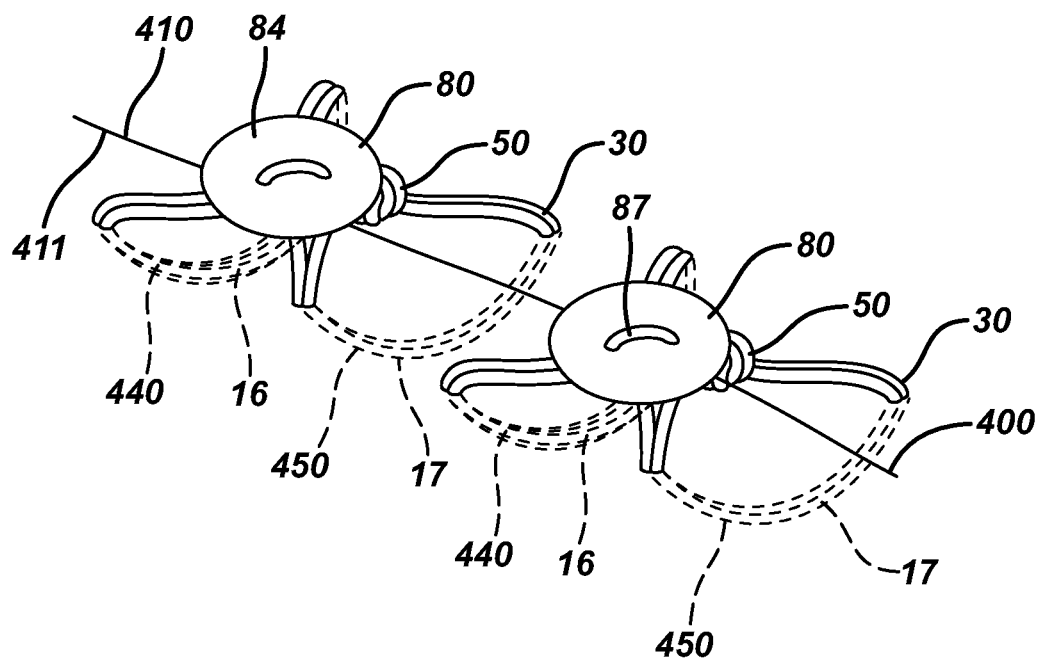

A surgical procedure that emplaces a cross-stitch (also known as cross mattress suture, X-mattress suture and cruciate suture) about a wound in tissue is illustrated in FIGS. 14-19. This procedure as illustrated utilizes devices 10 of the present invention. The procedure is similar to that for an interrupted stitch as described above, except that after a first suture pathway 440 is created by the surgeon, the surgeon creates a second pathway 450 adjacent to pathway 440 by once again rotating needle 90 through tissue 405 about the wound 400. After the second pathway 450 is created, the surgeon applies tension to the device to assure that sides 410 and 411 are approximated. Next the surgeon proceeds as in the interrupted stitch procedure as described above to lock the suture in place by inserting the needle holder 430 through opening 65 in loop section 67 to grasp anchor member 80 and pull it back through opening 65, thereby locking the stitches 16 and 17. Once again excess suture strand 30 and needle 90 are cut away adjacent to a knot 50 as illustrated. The process is repeated with a second device 10 to provide a second cross-stitch and complete the procedure by approximating sides 410 and 411 of wound 400 as seen in FIG. 19 without the need to tie surgical knots.

Another advantage to the knotted suture devices of the present invention is that the knots, when in the tissue pathway with the suture, provide the suture with resistance to withdrawal and assist in providing an anchoring of the suture in a tissue pathway. This effect is somewhat similar to the effect seen with a barbed suture.

Although this invention has been shown and described with respect to detailed embodiments thereof, it will be understood by those skilled in the art that various changes in form and detail thereof may be made without departing from the spirit and scope of the claimed invention.

We claim:

1. A method of approximating a wound in tissue in a mammal, comprising:

I. providing a surgical suture device, comprising:
a suture strand having a first end and a second end, wherein the suture strand is doubled over to form two sections of the suture strand which are knotted together to form a plurality of spaced apart knots to create a plurality of suture loops separated by the knots including an end loop, wherein each suture loop has an opening and first and second suture sections defining the opening together with at least one of the knots;
a surgical needle mounted to at least one end of the suture strand; and,
an anchor member mounted to one of the suture loops for engaging another loop, the anchor member having at least one suture opening, wherein the anchor member comprises a substantially flat disc member having a top and a bottom;

II. moving the needle and suture through tissue about an opening in said tissue, said tissue having a top surface, such that the bottom of the anchor member engages the tissue; and, III. moving the anchor member completely through one of the suture loops adjacent to the opening in the tissue, thereby approximating at least a section of the opening and securing the suture without tying a knot, such that the bottom of the disc member is located on the top surface of the tissue, thereby forming an interrupted stitch.

2. The method of claim 1, wherein the suture strand is coated with a lubricous coating.

3. The method of claim 1, wherein the suture strand is coated with an antimicrobial coating.

4. The method of claim 1, wherein one end of the suture strand extends beyond the other end of the suture strand to form a lead suture segment that does not contain knots.

5. The method of surgical claim 1, wherein both the first end and the second end of the suture strand are mounted to the surgical needle.

6. The method of surgical claim 1, wherein the first suture section is longer than the second suture section.

7. The method of claim 1 wherein the suture strand comprises a monofilament construction.

8. The method of claim 1, wherein the suture strand comprises a multifilament construction.

9. The method of claim 1, wherein the anchor member is mounted to the end loop.

* * * * *